United States Patent [19]

Yoshinaga et al.

[11] Patent Number: 4,880,560

[45] Date of Patent: Nov. 14, 1989

[54] LACTIC ACID DERIVATIVE, LIQUID CRYSTAL COMPOSITION CONTAINING SAME AND LIQUID CRYSTAL DEVICE

[75] Inventors: Kazuo Yoshinaga, Machida; Kazuharu Katagiri, Tama; Kenji Shinjo, Yokohama, all of Japan

[73] Assignee: Canon Kabushiki Kaisha, Tokyo, Japan

[21] Appl. No.: 292,953

[22] Filed: Jan. 3, 1989

Related U.S. Application Data

[62] Division of Ser. No. 922,308, Oct. 23, 1986, Pat. No. 4,812,259.

[30] Foreign Application Priority Data

Nov. 1, 1985 [JP] Japan ................... 60-245709
Dec. 13, 1985 [JP] Japan ................... 60-280403

[51] Int. Cl.$^4$ .............. C07C 65/21; C07C 65/24; C09K 19/52; C09K 19/12
[52] U.S. Cl. .............. 252/299.01; 252/299.6; 252/299.66; 252/299.65; 252/299.67; 252/299.61; 252/299.68; 562/469; 562/473
[58] Field of Search .......... 252/299.01, 299.6, 299.66, 252/299.61, 299.65, 299.68, 299.67; 350/350 S, 350 R; 562/469, 473

[56] References Cited

U.S. PATENT DOCUMENTS

| | | | |
|---|---|---|---|
| 4,065,489 | 12/1977 | Steinstrasser et al. | 252/299.65 |
| 4,158,011 | 6/1979 | Inukai et al. | 252/299.67 |
| 4,556,727 | 12/1985 | Walba | 252/299.67 |
| 4,564,694 | 1/1986 | Hirai et al. | 252/299.66 |
| 4,613,209 | 9/1986 | Goodby et al. | 350/350 S |
| 4,705,874 | 10/1987 | Walba et al. | 252/299.01 |
| 4,775,223 | 10/1988 | Yoshinaga et al. | 252/299.01 |

*Primary Examiner*—Teddy S. Gron
*Assistant Examiner*—J. E. Thomas
*Attorney, Agent, or Firm*—Fitzpatrick, Cella, Harper & Scinto

[57] ABSTRACT

An optically active lactic acid derivative represented by the following formula (Ia) or (Ib):

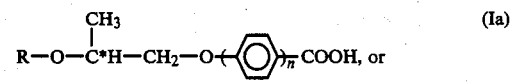

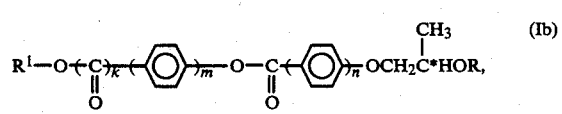

wherein
R is a linear, branched or cyclic saturated or unsaturated hydrocarbon group having 1–16 carbon atoms,
$R^1$ is an alkyl group having 4–16 carbon atoms,
m and n are respectively 1 or 2,
k is 0 or 1, and
C* is an asymmetric carbon atom.

A liquid crystal composition containing the lactic acid derivative and a liquid crystal device using the liquid crystal composition are also disclosed.

21 Claims, 8 Drawing Sheets

LACTIC ACID DERIVATIVE, LIQUID CRYSTAL COMPOSITION CONTAINING SAME AND LIQUID CRYSTAL DEVICE

This application is a division of application Ser. No. 922,308, filed Oct. 23, 1986, now U.S. Pat. No. 4,812,259.

FIELD OF THE INVENTION AND RELATED ART

The present invention relates to a lactic acid derivative capable of being readily modified with respect to its molecular structure and having an optical activity, a composition containing the lactic acid derivative, and also a liquid crystal device using the liquid crystal composition.

There has been known various types optical devices characterized by having optical activities as will be exemplified as follows:

(1) Those utilizing a cholesteric-nematic phase transition in a liquid crystal state (J. J. Wysoki, A. Adams and W. Haas: Phys. Rev. Lett., 20, 10204 (1968);

(2) Those utilizing a guest-host effect of the White-Taylor type in a liquid crystal state (D. L. White and G. N. Taylor: J. Appl. Phys., 45, 4718 (1974));

(3) Those utilizing a ferroelectric liquid crystal effect of a chiral smectic C phase, H phase, F phase, I phase or G phase (N. A. Clark and S. T. Lagerwall: Appl. Phys. Lett., 36 899 (1980)):

(4) Others including notch filters or band path filters utilizing selective scattering characteristics of a material having a cholesteric phase in the liquid crystal state when fixed in a matrix (F. J. Kahn: Appl. Phys. Lett., 18, 231 (1971)): and circular polarization beam slitters utilizing circular polarization characteristics (S. D. Jacobs, SPIE, 37, 98 (1981)).

These optical devices are important as display devices and modulation devices, while the explanation of the indiviudal systems is left to the respective references and omitted.

Functional materials constituting these optical devices contain an optically active compound or substance as a major component thereof or as a component which is used in a relatively small proportion but constitutes a functionally important part. Many of such optically active functional compounds are synthesized through an intermediate which per se is optically active.

Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives.

However, these intermediates involve respective problems as follows. Thus, optionally active chain hydrocarbon derivatives are difficult to modify their structures and very expensive except for a particular class thereof. Amino acid derivatives are relatively cheap and easy to modify their structures, whereas N-hydrogens therein are chemically active and liable to cause hydrogen bonding or other chemical reactions so that the performances of the resultant functional material can be restricted thereby. Camphor derivatives and cholesterol derivatives are difficult to modify the structures and the steric hindrance is liable to provide ill effects to the performances of the resultant functional materials.

Further, for a class of optical devices utilizing an electric field-responsive optical effect in a liquid crystal state, it has been practiced to introduce a polar group, whereas most of the above mentioned conventionally optically active intermediates has a small polarity or have a structure where the polar group cannot be effectively utilized.

It has been especially known for a ferroelectric liquid crystal that the response speed is proportional to its spontaneous polarization, so that it is desired to increase the spontaneous polarization for achieving a high speed driving. From such a viewpoint, P. Keller et al have shown that it is possible to realize a higher response speed through increase in spontaneous polarization by introducing a chlorine atoms so as to be bonded to an asymmetric carbon atoms (C.R. Acad. Sc. Paris, 282 C, 639 (1976)). However, the chlorine atom bonded to the asymmetric carbon atom is chemically unstable and has a large atomic radius so that the stability of the liquid crystal phase is lowered. Accordingly, an improvement is still desired.

The problems as described above have provided great difficulties in developing various functional materials.

SUMMARY OF THE INVENTION

A principal object of the present invention is, in view of the above problems, to provide a useful optically active compound which not only is useful as an appropriate optically active intermediate but also provides a high stability and a large spontaneous polarization when synthesized into a mesomorphic compound; and a liquid crystal composition containing the same.

A specific object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146 (1964), and a liquid crystal composition containing at least one of such mesomorphic compounds.

A further object of the present invention is to provide a liquid crystal composition having improved electric field responsive characteristics such as a response speed especially used as a ferroelectric liquid crystal.

A further object of the present invention is to provide a compound showing a large spontaneous polarization when used as a ferroelectric liquid crystal because it has an oxygen atom adjacent to an asymmetric carbon atom.

A still further object of the present invention is to provide a compound capable of easily controlling the hydrophobic group and being stably formed into a film when applied to the LB (Langmuir-Blodgett) film process for preparing an accumulation of single molecular films.

First of all, the present invention provides an optically active lactic acid derivative represented by the formula (Ia):

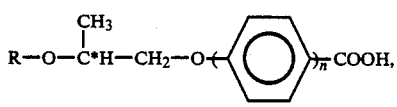

(Ia)

wherein

R is a linear, branched or cyclic saturated or unsaturated hydrocarbon group having 1–16 carbon n is 1 or 2, and C* is an asymmetric carbon atom; and also a lactic acid derivative obtained by using the above lactic acid derivative as an intermediate and represented by the formula (Ib):

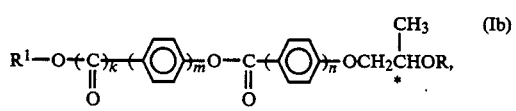

(Ib)

wherein $R^1$ is an alkyl group having 4–16 carbon atoms, R is the same as above, m and n are integers of 1 or 2, k is 0 or 1, and C* is an asymmetric carbon atom.

The present invention further provides a liquid crystal composition containing at least one species of the above mentioned lactic acid derivatives as a constituent, and a liquid crystal device using the same.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
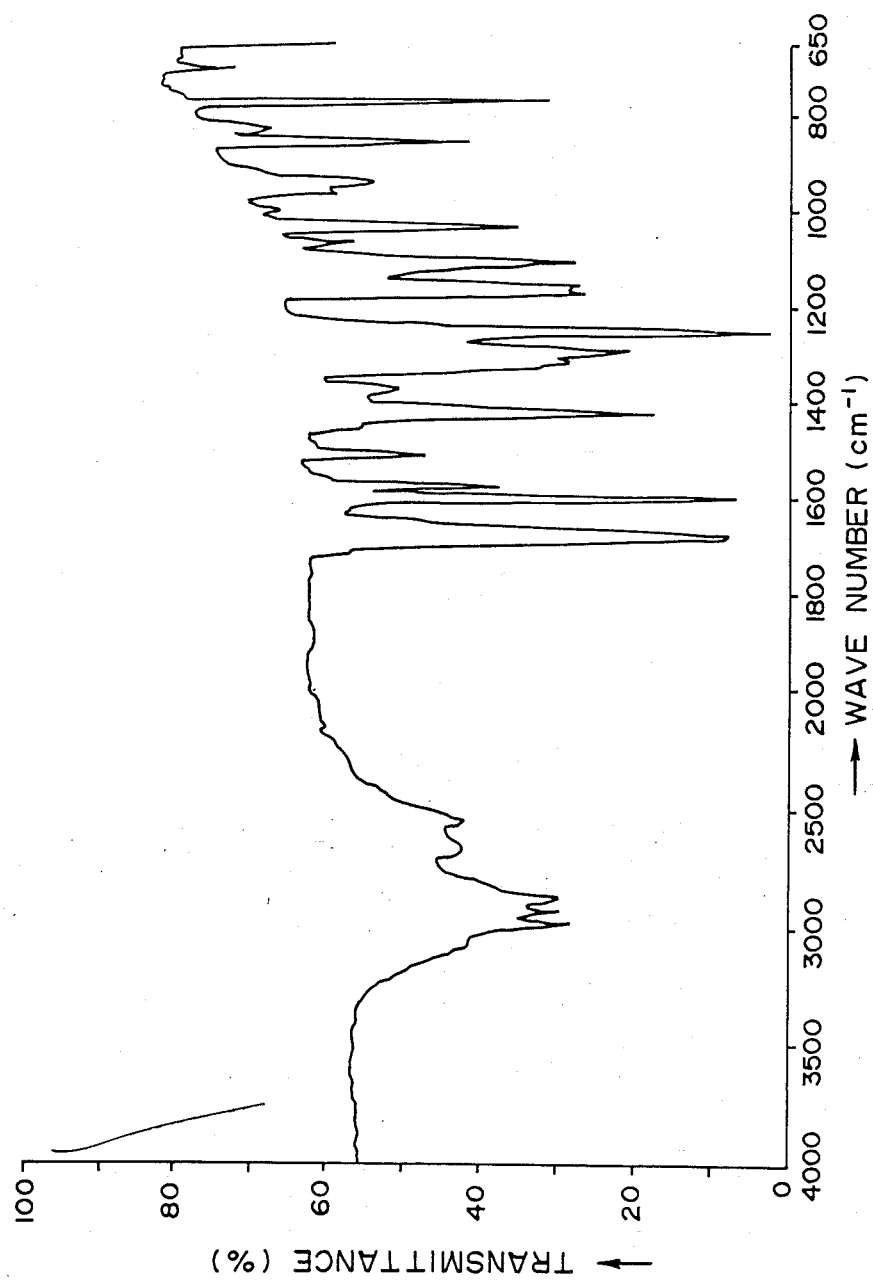
FIGS. 1–8 are infrared absorption charts of lactic acids obtained in Examples 1, 2, 5 and 8–12, respectively.

The compound represented by the above mentioned formula (Ia) has an asymmetric carbon atom and a reactive carboxyl group by the medium of a phenylene or biphenylene group and therefore its optical activity is very stable. For this reason, various derivatives may be synthesized from the compound through ester bonds, amide bonds, carbonate bonds, etc., without selecting particular reaction conditions. Further, the optical activity is not lost even when the carboxyl group is reduced or converted through a Grignard reaction. As the optical acivity is also stable even when the phenylene or biphenylene group is subjected to catalytic hydrogenation, the compound may be converted into a very wide variety of derivatives.

Further, the lactic acid derivative represented by the above formula (Ia) is not only a useful optically active intermediate as described above but also may be a useful liquid crystal component as it is. For example, when the compound is added in a very small amount to a nematic liquid crystal composition for use in a twisted nematic (TN) type display device, it may effectively be utilized to prevent the occurrence of a fringe pattern on a display face (reverse domain) to increase the uniformity of the display.

As a result, the present invention also provides a liquid crystal composition containing at least one species of the optically active lactic acid derivatives represented by the above formula (Ia).

The lactic acid derivatives represented by the formula (Ia) of the present invention are those having group R which is a linear, branched or cyclic saturated or unsaturated hydrocarbon group having 1–16 carbon atoms. When the number of carbon atoms is 17 or more the resultant functional material obtained finally therefrom is caused to have an increased viscosity or mol volume. A preferred number of carbon atoms in R 2–14. Specific examples of the group R include line alkyls, branched alkyls, cycloalkyl, linear alkenyl branched alkenyls, cycloalkenyls, linear alkadienyl branched alkadienyls, cycloalkadienyls, linear alkatri nyls, branched alkatrienyls, linear alkynyls, branche alkynyls, and aralkyls.

In order to synthesize functional materials adapte for use in optical devices, modulation devices, etc., it effective to combine the optically active lactic ac derivative without impairing the optical activity wi an intermediate of functional material having an appr priate intermolecular force and shape and susceptible molecular control.

A procss for synthesizing the optically active lact acid derivative according to the present invention exemplified by the following reaction schemes:

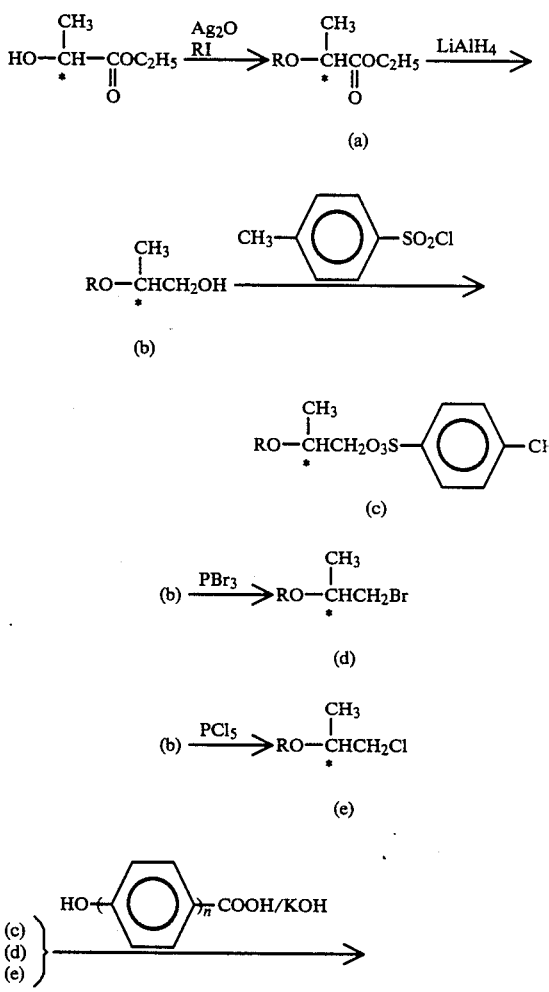

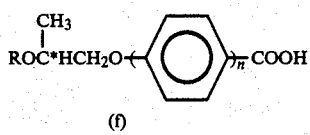

(f)

More specifically, a compound having an R of an alkyl group [compound of the above formula (a)] may be synthesized by reacting an lactic acid ester and a hydrocarbon iodide in the presence of Ag$_2$O. In this instance, it is preferred to place and mix the lactic acid ester and the hydrocarbon iodide in a vessel and then add Ag$_2$O to the mixture.

Further, in order to synthesized a compound of the above formula (b), a method of reacting the compound of the formula (a) with a reducing agent such as LiAlH$_4$.

The compound of the formula (b) may be further tosylated by reaction with p-toluenesulfonic acid chloride; or subjected to substitution of a halogen through a reaction with a halogenation agent such as PBr$_3$, SOCl$_2$, or PCl$_5$.

An optically active lactic acid derivative according to the present invention may be obtained by reacting the compound of the formula (c), (d) or (e) with p-hydroxybenzoic acid or p-hydroxybiphenylcarboxylic acid under an alkaline condition.

The optically active lactic acid derivatives represented by the formula (Ia) of the present invention may have a wide variety of R by changing the RI as a starting material, and particularly those having an R of 1–16 carbon atoms. Specific examples of the RI include linear saturated hydrocarbon iodides such as iodubutane, iodopentane, iodohexane, iodoheptane, iodooctane, iodononane, iododecane, iodoundecane, iodododecane, iodotridecane, iodotetradecane, iodopentadecane, idodhexadecane, iodoheptadecane, iodooctadecane, iodononadecane, and iodocicosane; branched saturated hydrocarbon iodides such as 2-iodobutane, 2-iodo-2-methylpropane and 1-iodo-3-methylbutane; cyclic unsaturated hydrocarbon iodides such as iodobenzyl, iodophenacyl and 3-iodo-1-cyclohexane; and cyclic saturated hydrocarbon iodides such as iodocyclopentane, iodocyclohexane, 1-iodo-3-methylcyclohexane, iodocycloheptane and iodocyclooctane.

Some examples of the optically active lactic acid derivative represented by the formula (Ia) of the present invention are shown in the following Table 1 together with their optical rotation data.

TABLE 1

| R | n | Optical rotation (c = 1, chlorform) | Example |
|---|---|---|---|
| C$_2$H$_5$— | 1 | −18.3° | 1 |
| C$_8$H$_{17}$— | 1 | −14.9° | 2 |
| C$_{12}$H$_{25}$— | 1 | −12.6° | 3 |
| C$_{16}$H$_{33}$— | 1 | −11.4° | 4 |
| C$_{12}$H$_{25}$— | 2 | −25.2° | 5 |
| C$_5$H$_{11}$— | 2 | −29.2° | 6 |

The optically active lactic acid derivative represented by the formula (Ia), as described before, may be used instead of conventional optically active intermediates such as chain hydrocarbon derivatives, amino acid derivatives, camphor derivatives, cholesterol derivatives, etc., to be combined with another intermediate through an ester bond, amide bond, carbonate bond, etc., by utilizing its carboxyl group. Accordingly, the compound not only is useful as an intermediate for producing functional materials constituting optical devices, but also may be used as an intermediate for synthesizing various natural optically active substances.

Further, the optically active lactic acid derivative represented by the formula (Ia) is effective for preventing the occurrence of reverse domain in a TN cell when added to nematic liquid crystal. In this case, the lactic acid derivative is preferably added in a proportion of 0.1–50 wt. % of the resulting liquid crystal composition.

Further, the lactic acid derivative may be added to a nematic liquid crystal to form a chiral nematic liquid crystal composition for use in a phase-transition type liquid crystal device or a composition for use in a White-Taylor type guest-host liquid crystal device. In this case, the lactic acid derivative may preferably be used in a proportion of 0.1–80 wt. % of the resultant liquid crystal composition.

Further, the lactic acid derivative may be added to a liquid crystal composition which per se shows a ferroelectric chiral smectic liquid crystal state in a proportion of 0.1 to 80 wt. % to improve the characteristics such as durability. Further, the lactic acid derivative may be added to smectic liquid crystals such as those having an ester unit, biphenylcarboxylate unit, azoxybenzene unit, pyrimidine ring, or phenylbenzoate unit including those of the formulas (1)–(5) shown below together with their phase transition temperatures (°C.) to provide liquid crystal compositions showing a ferroelectric chiral smectic phase. In this case, the lactic acid derivative may preferably be added in a proportion of 0.1–80 wt. % of the resultant liquid crystal composition.

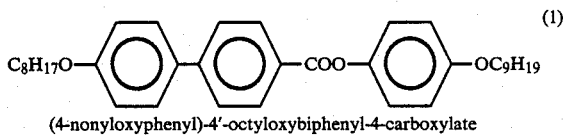

(4-nonyloxyphenyl)-4'-octyloxybiphenyl-4-carboxylate

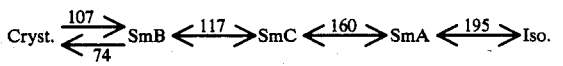

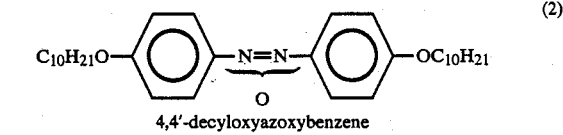

4,4'-decyloxyazoxybenzene

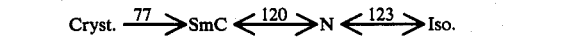

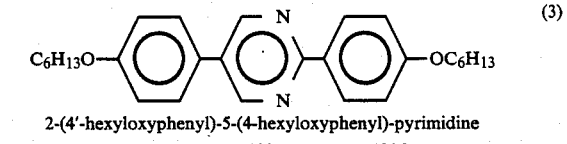

2-(4'-hexyloxyphenyl)-5-(4-hexyloxyphenyl)-pyrimidine

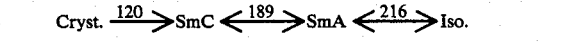

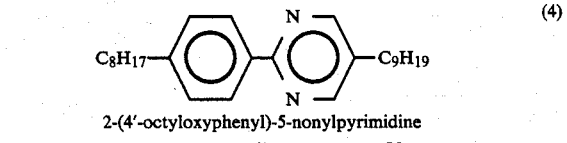

2-(4'-octyloxyphenyl)-5-nonylpyrimidine

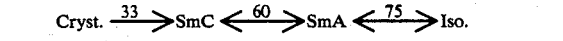

-continued

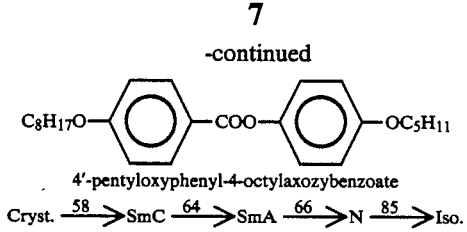

4'-pentyloxyphenyl-4-octylaxozybenzoate

Cryst. $\xrightarrow{58}$ SmC $\xrightarrow{64}$ SmA $\xrightarrow{66}$ N $\xrightarrow{85}$ Iso.

Herein, the symbols respectively denote the following phases:
Cryst.: crystal phase,
SmA: smectic A phase,
SmB: smectic B phase
SmC: smectic C phase,
N: nematic phase, and
Iso.: isotropic phase.

The optically active lactic acid derivatives repesented by the formula (Ib) are those having a group R which is linear, branched or cyclic saturated or unsaturated hydrocarbon group having 1–16 carbon atoms. The number of carbon atoms of 17 or more is undesirable because it provides a functional material having an increased viscosity or molar volume. A preferred number of carbon atoms in R is 2–14. Specific examples of the group R include linear alkyls, branched alkyls, cycloalkyls, linear alkenyls, branched alkenyls, cycloalkenyls, linear alkadienyls, branched alkadienyls, cycloalkadienyls, linear alkatrienyls, branched alkatrienyls, linear alkynyls, branched alkynyls, and aralkyls. In order to provide good liquid crystal characteristics, alkyl groups are especially preferred.

$R^1$ is an alkyl group having 4–16 carbon atoms, and the preferred number of carbon atoms in R is 6–14. Further, in the formula (Ib), m and n are respectively 1 or 2, and k is 0 or 1.

A process for synthesizing the optically active lactic acid derivative represented by the formula (Ib) of the present invention is exemplified by the reaction scheme shown below. The optically active lactic acid derivative may preferably be synthesized through the optically active intermediate represented by the formula (Ia) (i.e., the compound represented by the above formula (f)) in the following manner.

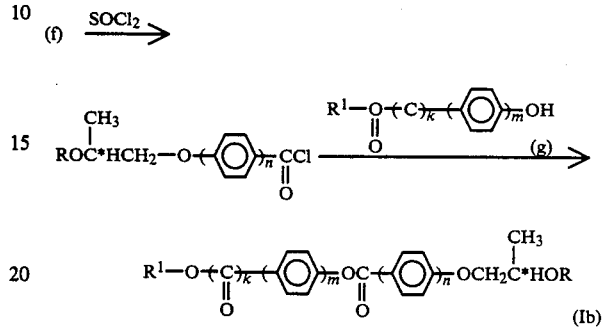

More specifically, the compound of the formula (f) may be reacted with a thionyl chloride to form an acid chloride, which is then reacted with a compound of the formula (g) above to obtain a compound of the formula (Ib), i.e., an optically active mesomorphic lactic acid derivative according to the present invention.

As a result, the lactic acid derivatives represented by the formula (Ib) may have a wide variety of R by changing the RI (iodides) used in preparation of the lactic acid derivatives of the formula (Ia).

Some examples of the optically actives represented by the formula (Ib) are shown in the following Table 2 together with their optical rotations and phase transition temperatures.

TABLE 2

$$R^1-O-(C)_k-\underset{O}{\parallel}-\left(\bigcirc\right)_{\overline{m}}OC-\underset{O}{\parallel}-\left(\bigcirc\right)_{\overline{n}}OCH_2\overset{*}{C}HOR$$
$$\hspace{3cm}\underset{CH_3}{\mid}$$

| Example | R | n | $R^1$ | m | k | Phase transition temp. | Optical rotation D (c = 1, chloroform) |
|---|---|---|---|---|---|---|---|
| 8 | $C_2H_5-$ | 1 | $C_8H_{17}-$ | 1 | 0 | Cryst. $\xrightarrow{35}$ Iso. ; $\xrightarrow{11}$ ; $\xrightarrow{19}$ ; SmA $\xrightarrow{16}$ Ch. | −12.0° |
| 9 | $C_8H_{17}-$ | 1 | $C_8H_{17}-$ | 1 | 0 | Cryst. $\xrightarrow{43}$ Iso. ; $\xrightarrow{11}$ ; $\xrightarrow{16}$ ; SmI | −10.4° |
| 10 | $C_{12}H_{25}-$ | 2 | $C_8H_{17}-$ | 1 | 0 | Cryst. $\underset{74}{\rightleftarrows}$ SmC* $\xrightarrow{116}$ SmA $\underset{115}{\overset{118.5}{\rightleftarrows}}$ Ch. $\underset{116}{\overset{119}{\rightleftarrows}}$ Iso. | −12.0° |
| 11 | $C_2H_5-$ | 1 | $C_{10}H_{21}-$ | 1 | 1 | Cryst. $\underset{-11}{\overset{31}{\rightleftarrows}}$ Iso. | −10.1° |

TABLE 2-continued

R¹—O(—C—)ₖ—〈◯〉ₘ—OC—〈◯〉ₙ—OCH₂CHOR
            ‖                ‖              |
            O                O            CH₃
                                            *

| Example | R | n | R¹ | m | k | Phase transition temp. | Optical rotation D (c = 1, chloroform) |
|---|---|---|---|---|---|---|---|
| 12 | $C_8H_{17}-$ | 1 | $C_{10}H_{21}-$ | 2 | 1 | Cryst. ←26.7— SmC* <br> ↖42.2  ↗47.1 <br> Sm1 <br> ←89.8— Iso. <br> —93.1→ | −9.6° |

*The numerals indicate temperatures in Celsius (°C.)

The liquid crystal composition according to the present invention may comprise at least one species of the optically active lactic acid derivative represented by the formula (Ib).

Especially, when the lactic acid derivative is added to a ferroelectric liquid crystal as represented by the formulas (6)–(18) shown below together with their phase transition temperatures (°C.), it is possible to increase the spontaneous polarization and to increase the response speed in combination with an effect of lowering the viscosity of the liquid crystal composition. In such a case, the mesomorphic lactic acid derivative represented by the formula (Ib) may preferably be added in an amount of 0.1–99 wt. %, particularly 1–90 wt. % of the resultant liquid crystal composition.

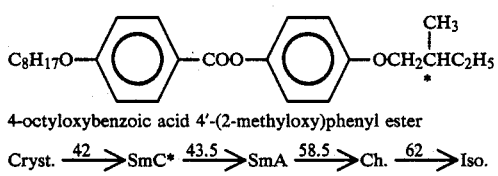

(6)

4-octyloxybenzoic acid 4'-(2-methyloxy)phenyl ester

Cryst. —42→ SmC* —43.5→ SmA —58.5→ Ch. —62→ Iso.

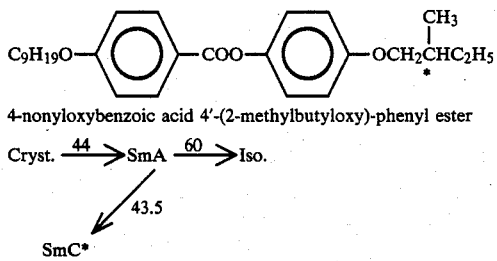

(7)

4-nonyloxybenzoic acid 4'-(2-methylbutyloxy)-phenyl ester

Cryst. —44→ SmA —60→ Iso.
       ↘43.5
       SmC*

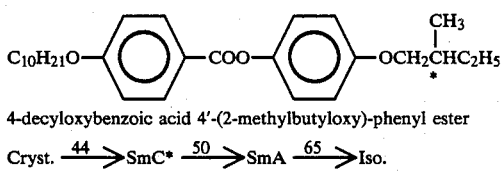

(8)

4-decyloxybenzoic acid 4'-(2-methylbutyloxy)-phenyl ester

Cryst. —44→ SmC* —50→ SmA —65→ Iso.

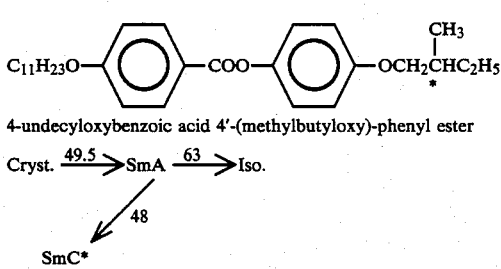

(9)

4-undecyloxybenzoic acid 4'-(methylbutyloxy)-phenyl ester

Cryst. —49.5→ SmA —63→ Iso.
        ↘48
        SmC*

-continued

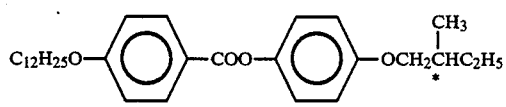
(10)
4-dodecyloxybenzoic acid 4'-(2-methylbutyloxy)-phenyl ester

Cryst. $\xrightarrow{49}$ SmC* $\xrightarrow{52}$ SmA $\xrightarrow{65}$ Iso.

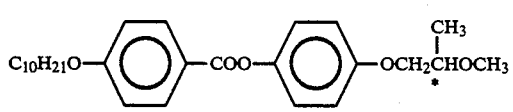
(11)
4-decyloxybenzoic acid 4'-(2-methylbutyloxy)-phenyl ester

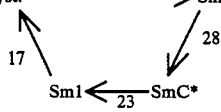

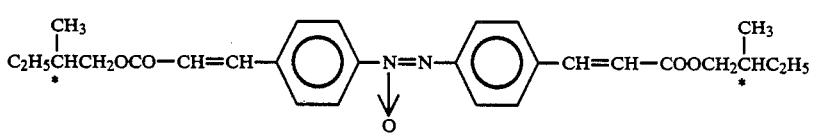
(12)
4,4'-azoxycinnamic acid bis(2-methylbutyl) ester

Cryst. $\underset{121}{\rightleftarrows}$ SmC* $\underset{134}{\rightleftarrows}$ SmA $\underset{168}{\rightleftarrows}$ Iso.

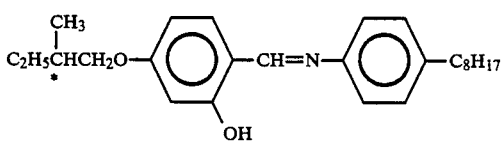
(13)
4-o-(2-methyl)butylresorcylidene-4'-octylaniline (MBRA (8))

Cryst. $\underset{28}{\rightleftarrows}$ SmC* $\underset{55}{\rightleftarrows}$ SmA $\underset{62}{\rightleftarrows}$ Iso.

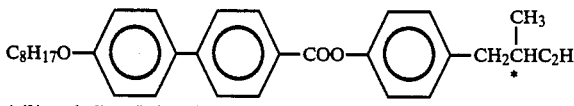
(14)
4-(2'-methylbutyl)phenyl 4'-octyloxybiphenyl-4-carboxylate

Cryst. $\underset{78}{\rightleftarrows}$ Sm3 $\underset{80}{\rightleftarrows}$ SmC* $\underset{128.3}{\rightleftarrows}$ SmA $\underset{171.0}{\rightleftarrows}$ Ch. $\underset{174.2}{\rightleftarrows}$ Iso.

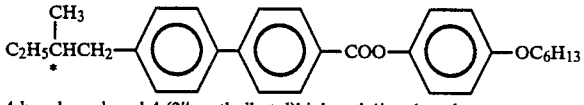
(15)
4-hexyloxyphenyl 4-(2''-methylbutyl)biphenyl-4'-carboxylate

Cryst. $\underset{68.8}{\rightleftarrows}$ SmC* $\underset{80.2}{\rightleftarrows}$ Ch. $\underset{163.5}{\rightleftarrows}$ Iso.

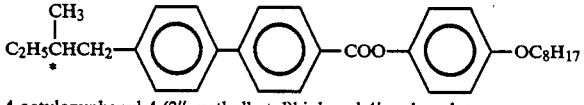
(16)
4-octyloxyphenyl 4-(2''-methylbutyl)biphenyl-4'-carboxylate

Cryst. $\underset{76}{\rightleftarrows}$ SmC* $\underset{88.6}{\rightleftarrows}$ Ch. $\underset{155.4}{\rightleftarrows}$ Iso.

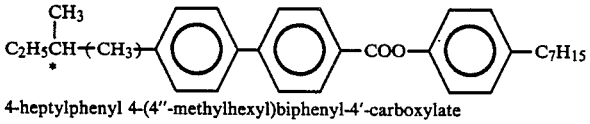
(17)
4-heptylphenyl 4-(4''-methylhexyl)biphenyl-4'-carboxylate

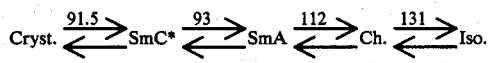

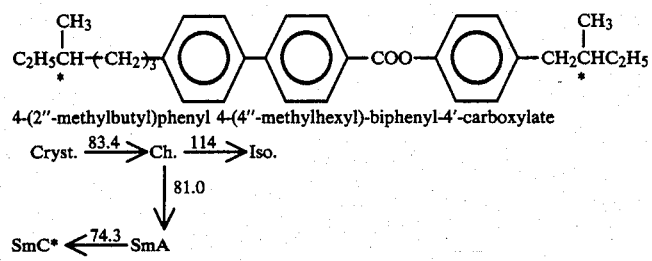

4-(2″-methylbutyl)phenyl 4-(4″-methylhexyl)-biphenyl-4′-carboxylate

Further, the optically active lactic acid derivative represented by the formula (Ib) may be mixed with a smectic liquid crystal which per se is not chiral to provide a composition which can be used as a ferroelectric liquid crystal. In such a case, the lactic acid derivative may be used in a proportion of 1.0–99 wt. % of the resultant liquid crystal composition.

Further, the lactic acid derivative may also be used as a component of a nematic liquid crystal composition for use in a TN type cell to prevent the occurrence of reverse domain.

As described above, the lactic acid derivative represented by the formula (Ia) of the present invention may be combined with an intermediate for a functional material without impairing the optical activity and may be susceptible of flexible molecular control. Further, a particular class of the lactic acid derivatives may change the length of the alkyl chain so that the kind of the liquid crystal phase and the temperature range for the liquid crystal state can be controlled to provide an excellent liquid crystal composition. The thus obtained mesomorphic compound and the liquid crystal composition containing at least one species thereof can effectively utilize a dipole moment originating from an oxygen atom because the oxygen atom is present adjacent to an asymmetric carbon atom. Particularly when used as a component of a ferroelectric liquid crystal, the lactic acid derivative can increase the spontaneous polarization and improve the electric field response characteristic including a response speed.

Further, the lactic acid derivative according to the present invention may be easily controlled with respect to its hdyrophobic group when it is used to form a unimolecular accumulation film according to the LB film process.

Furthermore, the lactic acid derivative according to the present invention, when incorporated as a component of a liquid crystal composition, can prevent the occurrence of reverse domain in a TN-type liquid crystal composition, or improve the characteristics of a chiral nematic liquid crystal or a chiral smectic liquid crystal.

The mesomorphic lactic acid derivative represented by the formula (Ib) may be obtained from the lactic acid derivative of the formula (Ia) through a combination with an appropriate functional intermediate, thus being susceptible of free molecular designing. Especially, through the selection of the length of the alkyl chain, the kind of the liquid crystal phase and the temperature range in the liquid crystal state can be controlled. Further, a liquid crystal composition containing at least one species of the optically active lactic acid derivative may be used as a chiral nematic liquid crystal or chiral smectic liquid crystal having improved performances such as prevention of reverse domain or improved response speed through increased spontaneous polarization or controlled viscosity.

Hereinbelow, the present invention will be explained more specifically with respect to optically active lactic acid derivatives, liquid crystal composition containing the same and liquid crystal devices using the same.

EXAMPLE 1

P-(2-ethoxy)propyloxybenzoic acid 10 g of 2-ethoxypropanol was dissolved in 59 ml of pyridine and the solution was cooled to below 5° C. To the solution under stirring was added 22 g of p-toluene sulfonic acid chloride. After that, the mixture was stirred for 5 hours at room temperature and left standing overnight. Cold water was added thereto, and the mixture was subjected to extraction with ether. The ether extract was washed with water, followed by distilling off of the ether to obtain 24 g of p-toluenesulfonic acid 2-ethoxypropyl ester.

10.7 g of p-hydroxybenzoic acid was dissolved in 8 ml of ethanol, and into the solution were added 10.2 g of 85% of KOH and 12 ml of water under stirring. To the mixture was added dropwise 24 g of the above obtained p-toluenesulfonic acid 2-ethoxypropyl ester.

After the addition, the mixture was heated and refluxed for 10 hours. After the recovery of the ethanol 24 g of 10% KOH aqueous solution was added to the mixture, followed by refluxing for 2 hours. After cooling, 6N-hydrochloric acid was added to precipitate white crystal, which was then filtered out, washed with water and recrystallized from hexane to obtain 6 g of p-(2-ethoxy)propyloxybenzoic acid.

Optical rotation $[\alpha]_D - 18.3°$

EXAMPLES 2, 3 AND 4

P-(2-octyloxy)propyloxybenzoic acid (Example 2) p-(2-dodecyloxy)propyloxybenzoic acid (Example 3) and p-(2-hexadecyloxy)propyloxybenzoic acid (Example 4) were prepared in the same manner as in Example 1 except that the 2-ethoxypropanol was replaced by 2-octyloxypropanol, 2-dodecyloxypropanol and 2-hexadecylpropanol, respectively. The optical rotation data as shown in Table 1 described before were obtained.

EXAMPLE 5

P-(2-dodecyloxy)propyloxybiphenylcarboxylic acid.

10 g of 2-dodecyloxypropanol was dissolved in 25 ml of pyridine, the solution was cooled to below 5° C., and 9.4 g of p-toluenesulfonic acid chloride was added thereto. The mixture was stirred for 6 hours and left standing overnight. Cold water was added and the mixture was subjected to extraction with ether. The ether extract was washed with water, and the ether was recovered to obtain 16 g of p-toluenesulfonic acid 2-dodecyl oxypropyl ester. Into 37 ml of ethanol was added 7.2 g of 4-hydroxy-4'-biphenylcarboxylic acid, and 4.4 g of 85% KOH and 5.3 ml of water were added thereto. To the mixture was added dropwise 16 g of the above p-toluenesulfonic acid 2-dodedcyloxypropyl ester, and the mixture was refluxed for 10 hours. The ethanol was recovered from the mixture, and 10 g of 10% KOH aqueous solution was added to the remainder, followed by 2 hours of refluxing. After cooling, 6N-HCl aqueous solution was added to the mixture to precipitate a white crystal, which was then filtered out and washed with water. The crystal was recrystallized from ethanol to obtain 3.5 g of p-(2-dodecyloxy)propyloxybiphenylcarboxylic acid.

Optical rotation $[\alpha]_D - 25.2°$

EXAMPLE 6

4-(2-pentyloxy)propyloxy-4'-biphenylcarboxylic acid was prepared in the same manner as in Example 5 except that 2-pentyloxypropanol was used instead of 2-dodecyloxypropanol.

Figure 2:
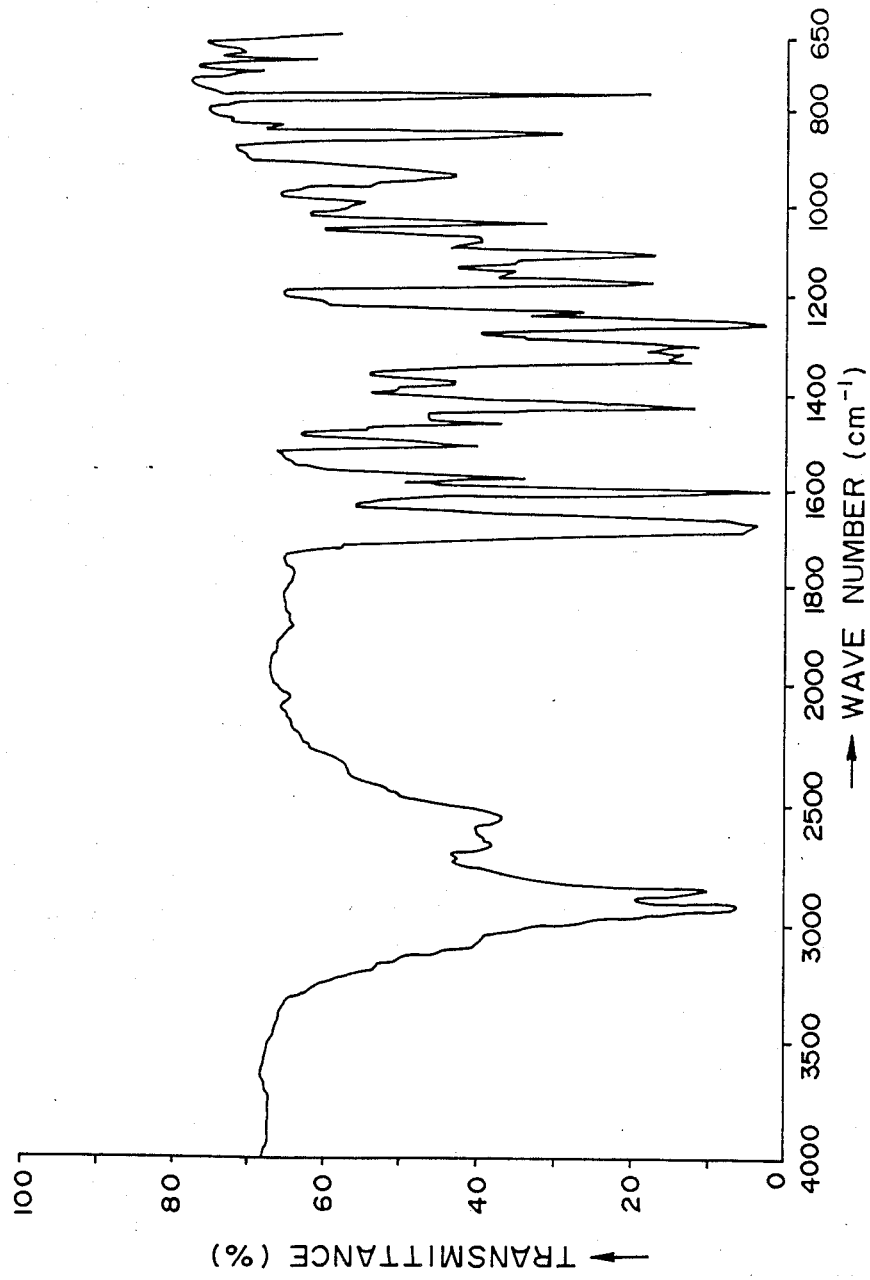
Figure 3:
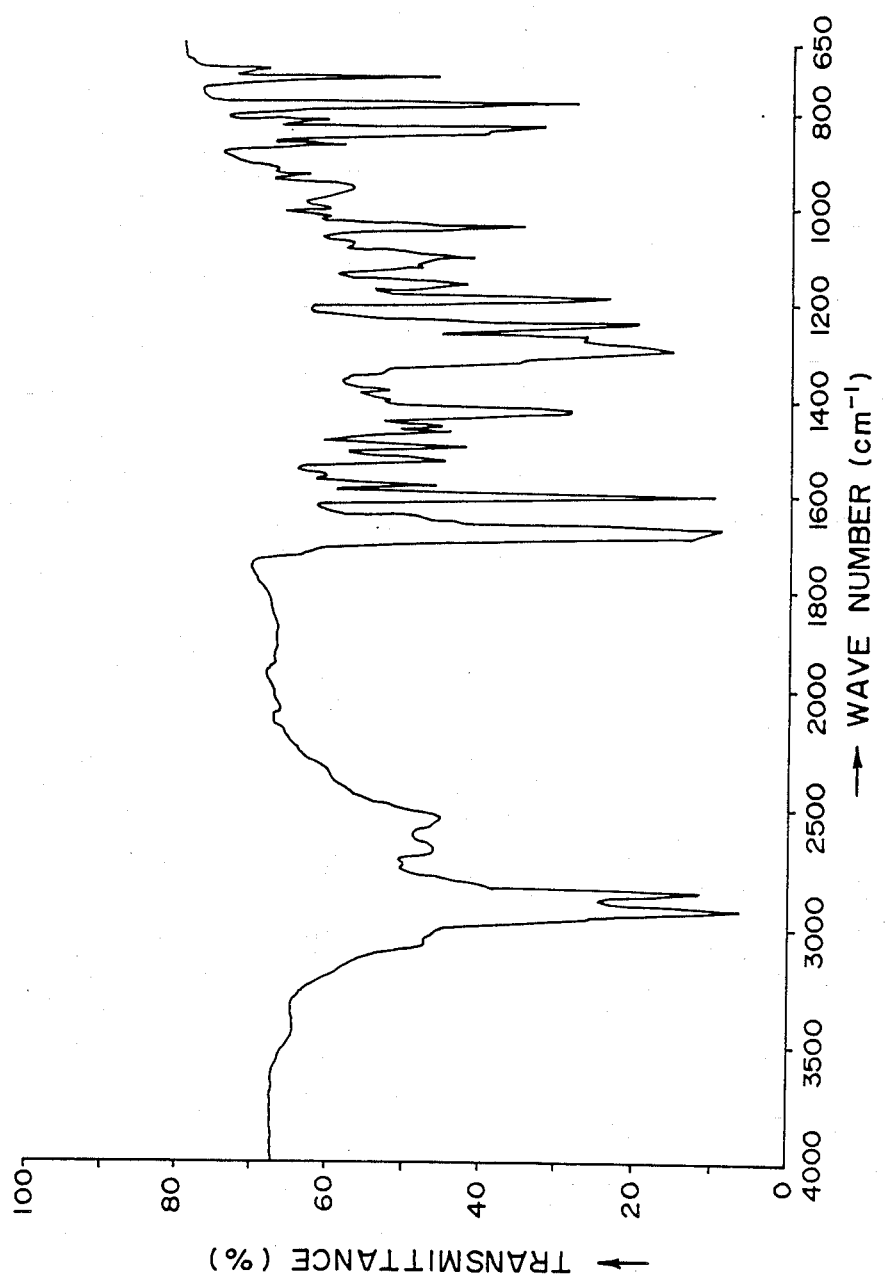

The optical rotation data of the lactic acid derivatives obtained in the above mentioned Examples are inclusively shown in Table 1 described before. Further, infrared absorption charts (KBr method) of the lactic acid derivative obtained in Examples 1, 2 and 5 are shown in FIGS. 1–3, respectively.

EXAMPLE 7

A liquid crystal mixture was prepared by adding 2 wt. parts of p-(2-dodecyloxy)propyloxybiphenylcarboxylic acid obtained in Example 5 to 98 wt. parts of p,p'-pentylazoxybenzene. A TN cell (twisted nematic cell) using the liquid crystal mixture was observed to show remarkably decreased reverse domain compared with a TN cell prepared without adding the compound of Example 5.

EXAMPLE 8

4-(2-ethoxypropyloxy)benzoic acid 4'-octyloxyphenyl ester.

5.1 ml of thionyl chloride was added to 1.5 g of 4-(2-ethoxypropyloxy)benzoic acid, and the mixture was refluxed for 2 hours. The thionyl chloride was distilled off and toluene was added to the remainder. To the mixture was added dropwise a solution of 1.5 g of p-octyloxyphenol in 7.7 ml of dry pyridine below 5° C. The mixture was stirred for 3.5 hours at room temperature and left standing overnight. Cold water was added thereto, and the mixture was subjected to extraction with ether. The ether extract was washed with 5% HCl aqueous solution, 5% NaOH aqueous solution and further with water. The solvent was distilled off, and the product was purified by silica gel column chromatography to obtain 1.2 g of 4-(2-ethoxypropyl)benzoic acid 4'-octyloxyphenyl ester.

The product showed the following infrared absorption peaks:

IR (cm$^{-1}$): 2940, 1735, 1605, 1510, 1250, 1190, 1165, 1070.

Figure 4:
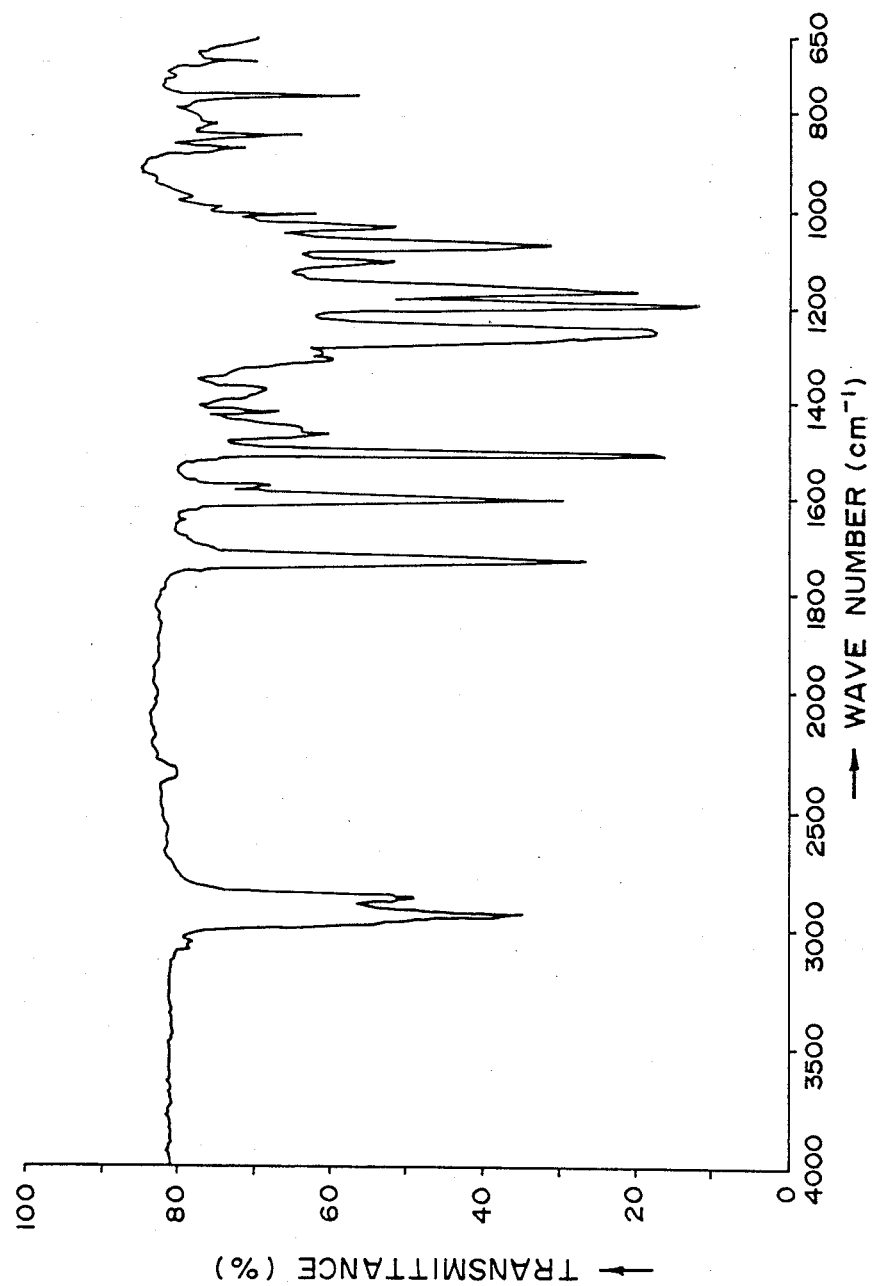

The IR absorption chart is shown in FIG. 4.

EXAMPLE 9

4-(2-octyloxypropyloxy)benzoic acid 4'-octyloxyphenyl ester was prepared in the same manner as in Example 8 by using 4-(2-octyloxypropyloxy)benzoic acid instead of the 4-(2-ethoxypropyloxy)benzoic acid.

The product showed the following infrared absorption peaks:

IR (cm$^{-1}$): 2930, 1715, 1600, 1510, 1470, 1270, 1190, 1175, 1100, 1075.

Figure 5:
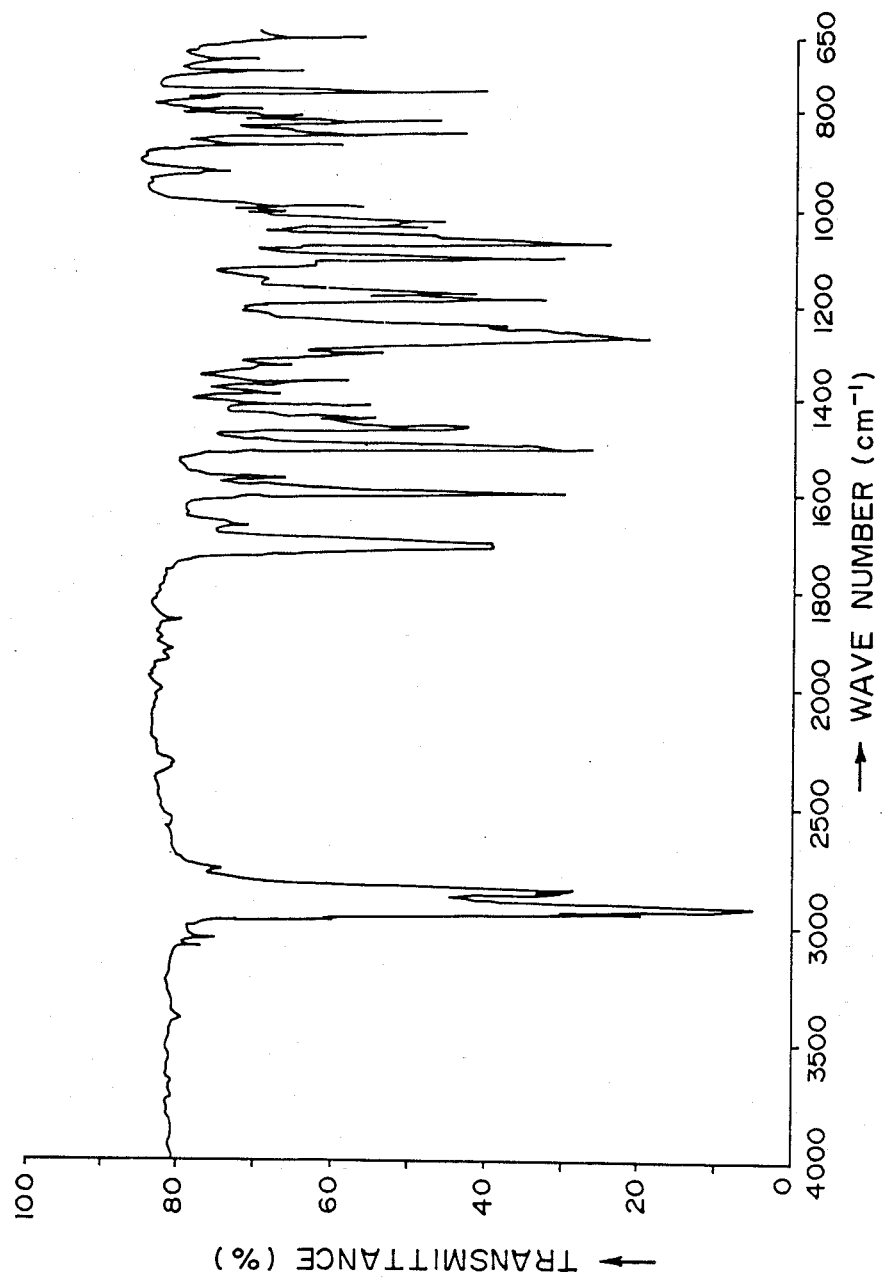

The IR absorption chart is shown in FIG. 5.

EXAMPLE 10

4-(2-dodecyloxypropyloxy)biphenylcarboxylic acid octyloxyphenyl ester.

To 2.0 g of 4-(2-dodecyloxypropyloxy)biphenylcarboxylic acid were added 0.8 g of phosphorus pentachloride and further 3.9 ml of phosphorus oxychloride, and the mixture was refluxed for 2 hours. The phosphorus oxychloride was distilled off from the reaction product, and toluene was added thereto. To the mixture was added dropwise 1.0 g of 4-octyloxyphenol dissolved in 6.1 ml of pyridine. The mixture was stirred for 2.5 hours at room temperature and left standing overnight. Cold water was added thereto and the mixture was subjected to extraction with ether. The ether extract washed with water and the solvent was distilled off. The remainder was purified by silica gel chromatography to obtain 1.3 g of 4-(2-dodecyloxypropyloxy)biphenylcarboxylic acid octyloxyphenyl ester.

Figure 6:
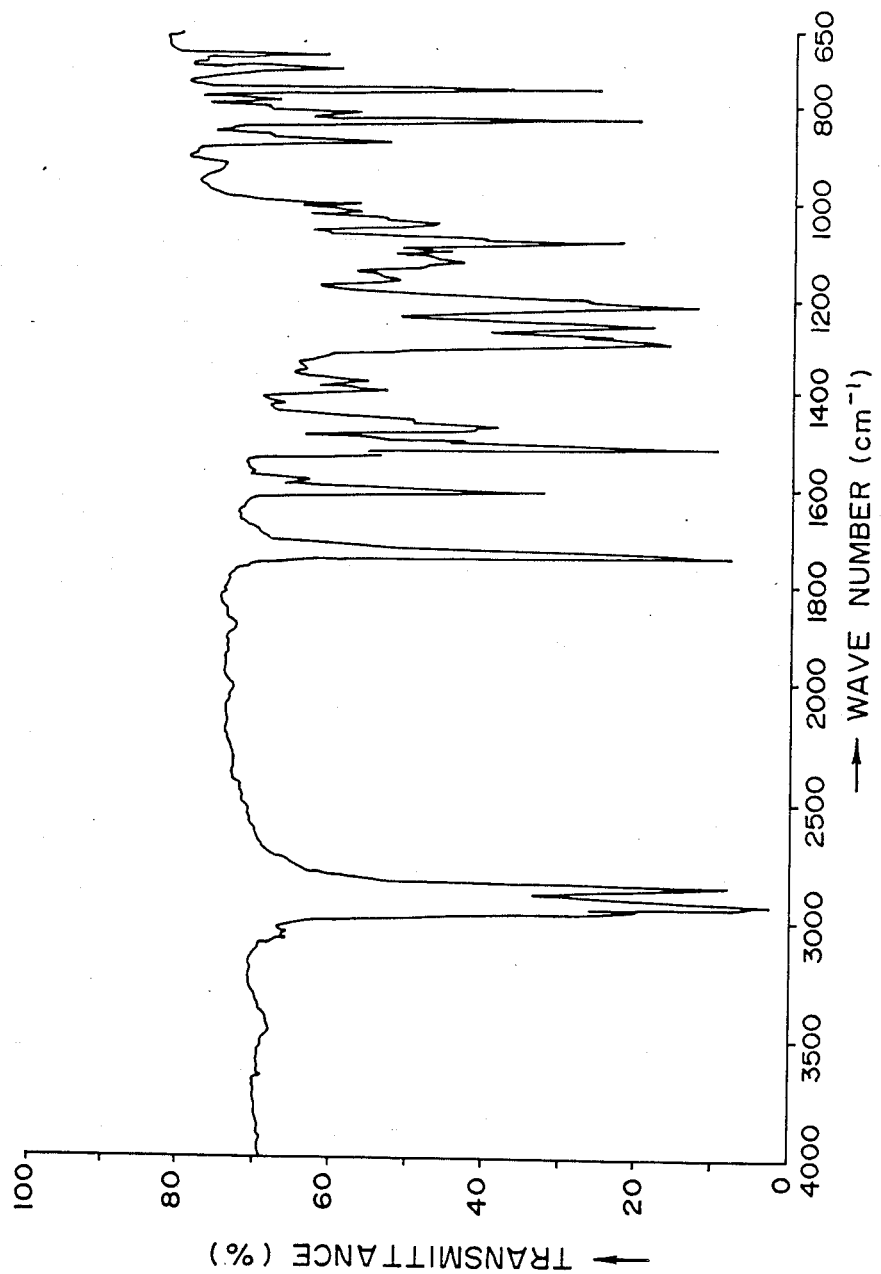

The IR absorption chart of the product is shown in FIG. 6.

EXAMPLE 11

4-(2-ethoxypropyloxy)benzoic acid 4'(decyloxycarbonyl)phenyl ester was prepared from 4-(2-ethoxypropyloxy)benzoic acid and 4-hydroxybenzoic acid decyl ester in the same manner as in Example 8.

The product showed the following infrared absorption peaks:

IR (cm$^{-1}$): 3930, 3855, 1735, 1720, 1600, 1510, 1250, 1200, 1160, 1105, 1060, 760.

Figure 7:
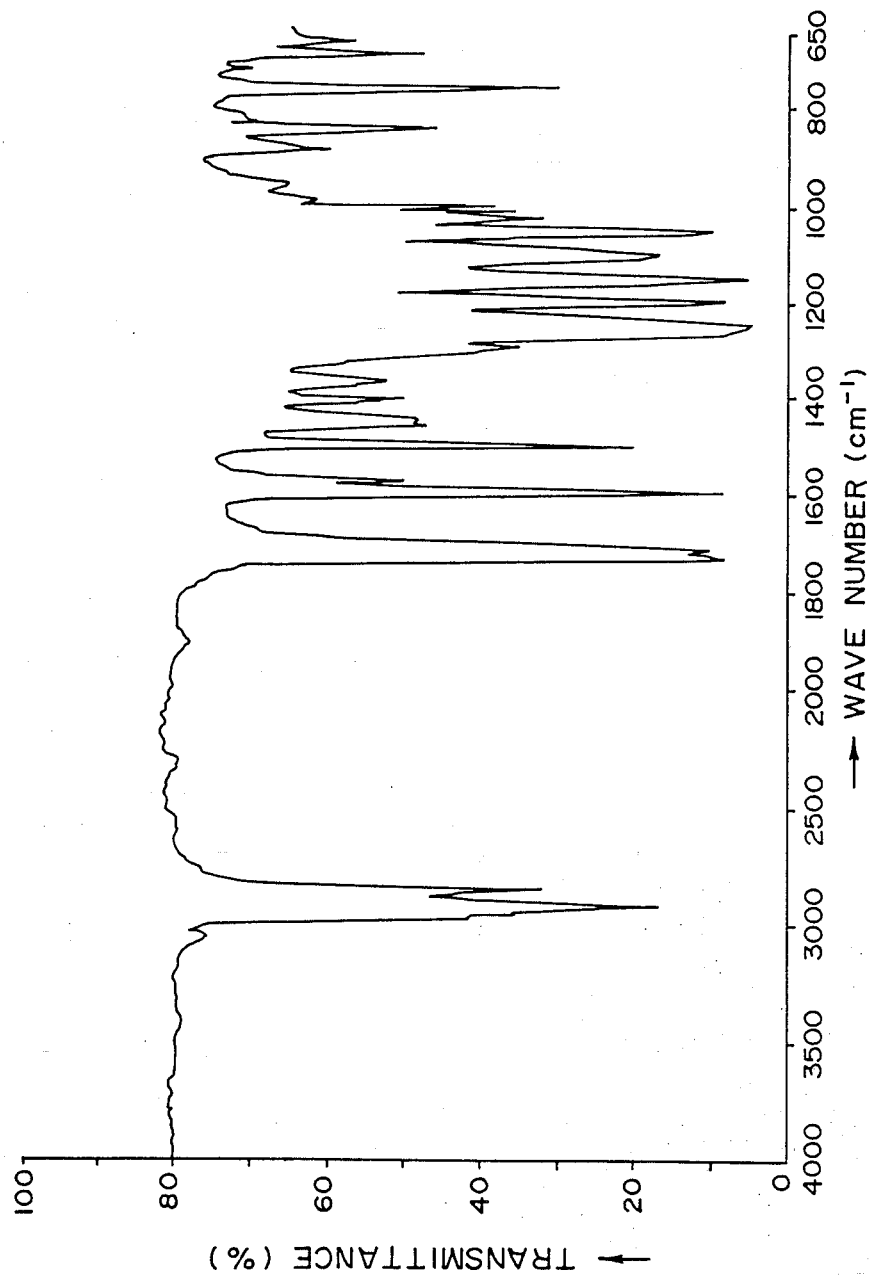

The IR absorption chart is shown in FIG. 7.

EXAMPLE 12

4-(2-octyloxypropyloxy)benzoic acid 4'-(decyloxycarbonyl)biphenyl ester was prepared from 4-(2-octyloxypropyloxy)benzoic acid an 4'-hydroxybiphenylcarboxylic acid decyl ester in the same manner as in Example 11.

The product showed the following IR absorption peaks:

(IR (cm$^{-1}$): 3930, 2850, 1730, 1710, 1600, 1510, 1280, 1170, 1110, 770.

Figure 8:
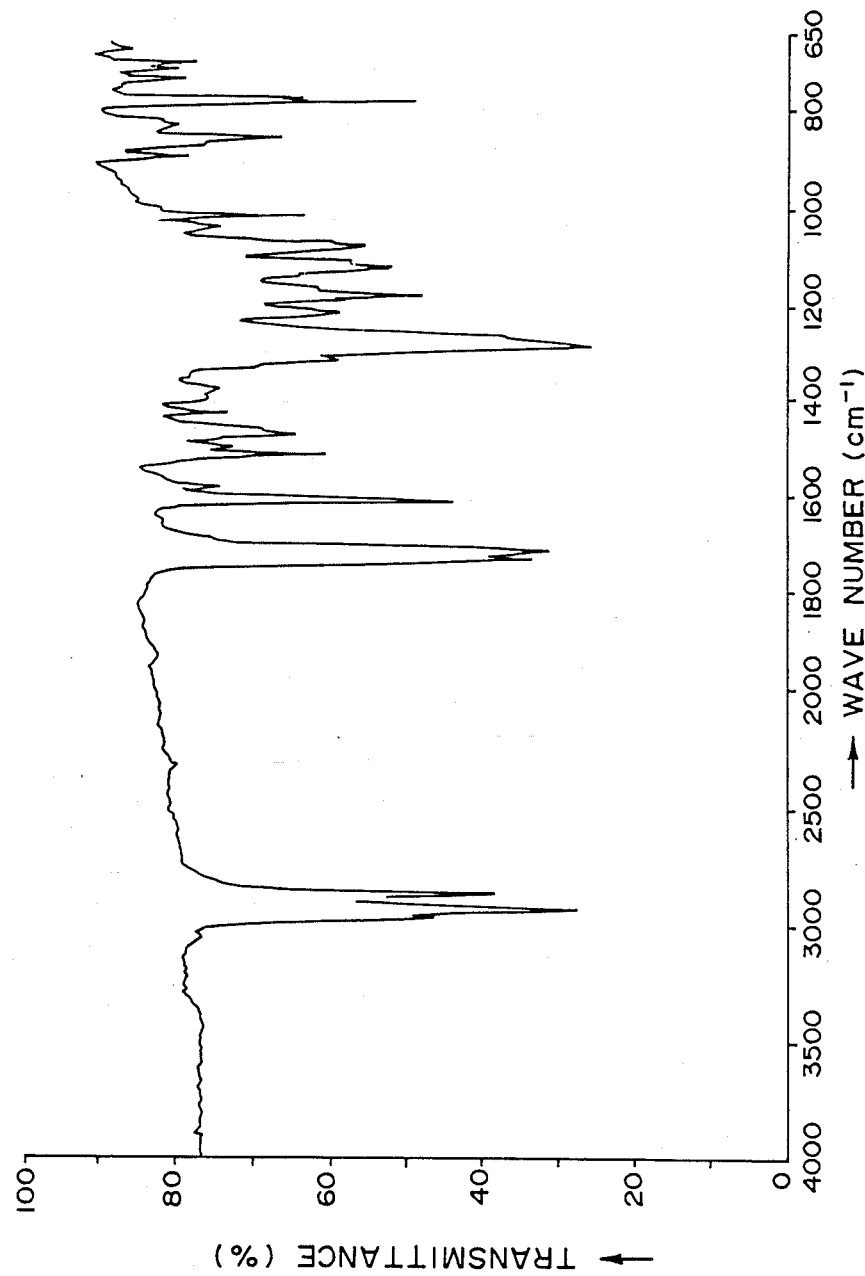

The IR absorption chart is shown in FIG. 8.

EXAMPLE 13

The following liquid crystal composition was prepared:

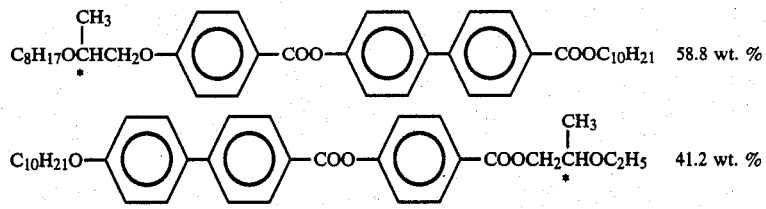

The liquid crystal composition showed SmC* phase in the temperature range of 102°–15° C. in the course of cooling. Thus, it was found that the inclusion of a mesomorphic lactic acid derivative according to the present invention could lower the temperature range for SmC* phase without narrowing the same.

EXAMPLE 14

A liquid crystal device using the liquid crystal composition prepared in Example 13.

An about 1000 Å-thick ITO film was formed as an electrode on a highly polished glass plate of 10×20 mm, and an SiO$_2$ film in a thickness of about 1000 Å was vapor-deposited by the ion-beam process. Onto another glass plate processed in the same manner, The liquid crystal composition prepared in Example 13 was dropped, and the above glass plate was superposed thereon. The glass plates were slided in parallel with each other at 115° C. while being pressed to each other to maintain a gap therebetween and being observed through a polarizing microscope, whereby a homogeneously aligned monodomain was obtained. The liquid crystal layer thickness at that time was about 1.0 μm. The liquid crystal placed in the chiral smectic C phase was subjected to application of ±20 V pulses, whereby switching was effected in about 500 μsec.

What is claimed is:

1. An optically active lactic acid derivative represented by the formula (Ia):

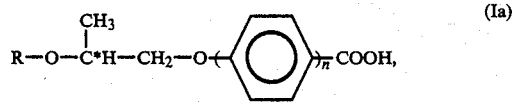

wherein
R is a linear alkyl group having 1–16 carbon atoms,
n is 1 or 2, and
C* is an asymmetric carbon atom.

2. A lactic acid derivative according to claim 1, wherein said R is a linear alkyl group having 2–14 carbon atoms.

3. A lactic acid derivative according to claim 1, which is represented by the formula:

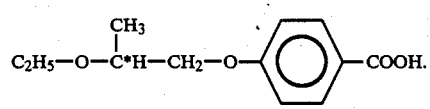

4. A lactic acid derivative according to claim 1, which is represented by the formula:

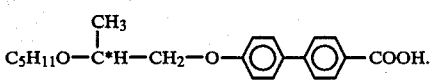

5. A lactic acid derivative according to claim 1, which is represented by the formula:

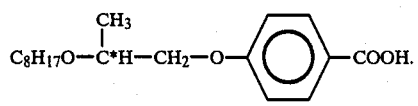

6. A lactic acid derivative according to claim 1, which is represented by the formula:

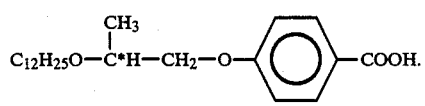

7. A lactic acid derivative according to claim 1, which is represented by the formula:

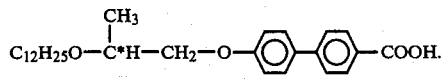

8. A lactic acid derivative according to claim 1, which is represented by the formula:

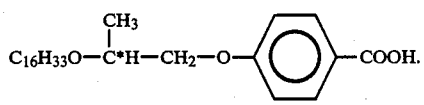

9. A liquid crystal composition containing at least one species of optically active lactic acid derivative represented by the formula (Ia):

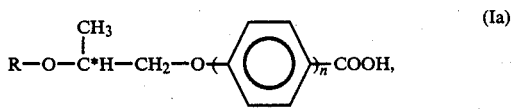

wherein
R is a linear alkyl group having 1–16 carbon atoms,
n is 1 or 2, and
C* is an asymmetric carbon atom.

10. A liquid crystal composition according to claim 9, which comprises a mixture of a lactic acid derivative represented by the formula (Ia) and a nematic liquid crystal.

11. A liquid crystal composition according to claim 10, which contains the lactic acid derivative in a proportion of 0.1-80 wt. %.

12. A liquid crystal composition according to claim 10, which contains the lactic acid derivative in a proportion of 0.1-50 wt. % and shows a nematic phase.

13. A liquid crystal composition according to claim 9, which comprises a mixture of a lactic acid derivative represented by the formula (Ia) and a smectic liquid crystal, and shows a chiral smectic phase.

14. A liquid crystal composition according to claim 13, which contains the lactic acid derivative in a proportion of 0.1-80 wt. %.

15. A liquid crystal composition according to claim 13, wherein said smectic liquid crystal is a compound having an ester unit.

16. A liquid crystal composition according to claim 13, wherein said smectic liquid crystal is a compound having a biphenylcarboxylate unit.

17. A liquid crystal composition according to claim 13, wherein said smectic liquid crystal is a compound having an azoxybenzene unit.

18. A liquid crystal composition according to claim 13, wherein said smectic liquid crystal is a compound having a pyrimidine ring.

19. A liquid crystal composition according to claim 13, wherein said smectic liquid crystal is a compound having a phenylbenzoate unit.

20. A liquid crystal composition according to claim 9, which comprises a mixture of a lactic acid derivative represented by the formula (Ia) and a chiral smectic liquid crystal, and shows a chiral smectic phase.

21. A liquid crystal composition according to claim 20, which contains the lactic acid derivative in a proportion of 0.1-80 wt. %.

* * * * *